US012318193B2

(12) United States Patent
Baxter et al.

(10) Patent No.: US 12,318,193 B2
(45) Date of Patent: Jun. 3, 2025

(54) APPARATUS AND ASSOCIATED METHODS FOR STEP LENGTH ESTIMATION

(71) Applicant: Waymap Limited, London (GB)

(72) Inventors: Paul Daniel Baxter, Cambridge (GB); Douglas James O'Rourke, Cambridge (GB)

(73) Assignee: Waymap Limited, London (GB)

( * ) Notice: Subject to any disclaimer, the term of this patent is extended or adjusted under 35 U.S.C. 154(b) by 659 days.

(21) Appl. No.: 17/627,710

(22) PCT Filed: Jul. 10, 2020

(86) PCT No.: PCT/GB2020/051679
§ 371 (c)(1),
(2) Date: Jan. 17, 2022

(87) PCT Pub. No.: WO2021/009499
PCT Pub. Date: Jan. 21, 2021

(65) Prior Publication Data
US 2022/0233100 A1    Jul. 28, 2022

(30) Foreign Application Priority Data

Jul. 17, 2019   (GB) .................................. 1910249

(51) Int. Cl.
*A61B 5/11*        (2006.01)
*A61B 5/00*        (2006.01)
*G01C 21/16*       (2006.01)

(52) U.S. Cl.
CPC ............. *A61B 5/112* (2013.01); *A61B 5/1118* (2013.01); *A61B 5/1126* (2013.01);
(Continued)

(58) Field of Classification Search
CPC ..... A61B 5/112; A61B 5/1118; A61B 5/1126; A61B 5/6801; A61B 5/725;
(Continued)

(56) References Cited

U.S. PATENT DOCUMENTS

2008/0105065 A1\*  5/2008  Lee ...................... A61B 5/6804
                                                                73/865.4
2013/0123669 A1    5/2013  Kinoshita et al.
(Continued)

FOREIGN PATENT DOCUMENTS

EP    2402715    1/2012
EP    3586742    1/2020
(Continued)

OTHER PUBLICATIONS

International Search Report and the Written Opinion Dated Sep. 17, 2020 From the International Searching Authority Re. Application No. PCT/GB2020/051679. (12 Pages).
(Continued)

*Primary Examiner* — David Z Huang

(57) ABSTRACT

A method and apparatus for estimating a step length of a user are disclosed. The method involves obtaining inertial data generated by an inertial sensor, extracting orthogonal motion components a plurality of directions, and estimating, based on the orthogonal motion components for each direction, a respective parameter that is indicative of energy expenditure by the user in the corresponding direction. The step length is then estimated, based on each estimated parameter indicating energy expenditure by the user, a corresponding step length.

19 Claims, 3 Drawing Sheets

(52) U.S. Cl.
CPC ............ *A61B 5/6801* (2013.01); *A61B 5/725* (2013.01); *G01C 21/16* (2013.01); *A61B 2562/0219* (2013.01)

(58) Field of Classification Search
CPC .......... A61B 2562/0219; A61B 5/6898; G01C 21/16; G01C 21/165; G01C 22/006
See application file for complete search history.

(56) References Cited

U.S. PATENT DOCUMENTS

2015/0211860 A1* 7/2015 Ohkubo .................... G01P 3/50
          702/142
2017/0265800 A1* 9/2017 Auchinleck .............. A61B 5/01

FOREIGN PATENT DOCUMENTS

WO  WO 2012/037577  3/2012
WO  WO 2015/0079260  6/2015

OTHER PUBLICATIONS

Patents Act 1977: Search Report Under Section 17 Dated Jan. 15, 2020 From the Intellectual Property Office of the United Kingdom of Great Britain Re. Application No. GB 1910249.0. (1 Page).
Wu et al. "A Survey of the Research Status of Pedestrian Dead Reckoning Systems Based on Inertial Sensors", International Journal of Automation and Computing, XP036710581, 16(1):65-83, Published Online Sep. 27, 2018.

* cited by examiner

APPARATUS AND ASSOCIATED METHODS FOR STEP LENGTH ESTIMATION

RELATED APPLICATIONS

This application is a National Phase of PCT Patent Application No. PCT/GB2020/051679 having International filing date of Jul. 10, 2020, which claims the benefit of priority of United Kingdom Patent Application No. 1910249.0 filed on Jul. 17, 2019. The contents of the above applications are all incorporated by reference as if fully set forth herein in their entirety.

FIELD AND BACKGROUND OF THE INVENTION

The present invention relates to step (or 'stride') length estimation and in particular apparatus and methods for step length estimation. The invention has particular although not exclusive relevance to step length estimation in devices mounted on a user's body, for example, on a user's waist or in a user's trouser or coat pocket.

It is now commonplace for mobile telephones and other portable computational devices to include location finding and related features, such as Global Positioning System (GPS) for tracking a user's position, and compasses in the form of magnetometers for direction finding. However, conventional location finding technology, such as GPS positioning, can be unreliable in some situations, in particular in environments where GPS signals cannot be received properly such as indoors, underground or in heavily forested areas. This can lead to situations where little or no location information can be derived for a user.

This issue is compounded by the many applications in which accurate location finding and/or tracking would be desirable in scenarios where the conventional location finding technology cannot be used with sufficient accuracy. One such application, for example, is the tracking of a device within a building or other GPS impaired location for the purposes of security, personnel or goods tracking, time-in-motion analysis and/or the like, in order to acquire information on current location, previous places visited, time spent in certain locations etc.

One technique for determining position in situations where conventional positioning technology cannot be used, or in which such use is undesirable, is so called 'dead reckoning' or 'ded ('deduced') reckoning' in which a previously 'known' position or 'fix' is used in combination with estimates of distance and direction travelled in order to estimate a current position. For example, inertial sensors (INS) of the sort commonly integrated into modern 'smart' devices including cellular phones (these are gyroscopes and multi-axis accelerometers) can be used, when supplemented with magnetometers, to provide, at a relatively low cost, motion data required for estimating indoor location. However, a significant limitation of such inertial sensing based dead reckoning is that the sensor measurements can be noisy and errors accumulate in the process of integrating the measured quantities to obtain the desired positional measurements (i.e. effectively integrating acceleration twice to obtain displacement and hence position).

Many existing solutions for indoor tracking therefore rely on some component of infrastructure, such as a ranging beacon, or knowledge of radio signal distribution from external infrastructure (e.g. cellular base stations) in the building, to alleviate this accumulation of error. This increases the cost and time required to set up such a system. Furthermore, there is the risk that elements of that infrastructure, such as the radio signal distribution, will change over time causing the associated positioning calculations to drift and hence a requirement for semi-regular re-calibration.

Other existing methodologies which make use of inertial data do so in a way which does not address the accumulation of error in inertial sensing. This may limit the applicability of such methods when deployed in realistic scenarios.

A system which helps to address many of these issues is described in international publication number, WO/2015/079260 which describes a particle filter based framework for indoor tracking and navigation, when GPS location is unavailable. The system fuses inertial measurement unit (IMU) with data from other sources including, for example, barometric data, beacon observations, and map data to provide a particularly effective form of Pedestrian Dead Reckoning (PDR) algorithm. In particular, the system makes use of a step-and-heading system (SHS) based on step detection, step length estimation (SLE), and step heading estimation.

Diez, L. E.; Bahillo, A.; Otegui, J.; Otim, T. Step Length Estimation Methods Based on Inertial Sensors: A Review. IEEE Sens. J. 2018, 18, 6908-6926 (Diez et. al.) discusses the importance, in PDR systems, of achieving accurate estimation of step length or stride length and how this is critical to obtaining good PDR performance and provides a fairly comprehensive covering of a wide range of techniques for step length estimation. These can be grouped by the source of their estimations as follows:

Biomechanical based estimation which uses an understanding of human biomechanics to derive a suitable estimator—often bringing in prior measurements (e.g. leg length) to improve the quality of the estimation. Specifically, many such biomechanical estimation based methods require measurement of something and transformation of the measurement result(s) in order to estimate step length. Typical measurements used are:

Vertical displacement of pelvis over the planted foot which requires knowledge of leg length.

Rate of stepping, which has been shown to be more consistent for an individual than within the whole population, and is also known to be affected significantly by slope and terrain.

Arm swing, which is popular for wrist mounted devices but which also has been found to have reduced accuracy compared, for example, to foot mounted sensors.

Direct integration based estimation of inertial sensor data in which double integration of acceleration data is used to calculate displacement. There appear to be only a few studies of this approach, with apparently limited success.

Statistical regression based estimation in which one or several features are measured for a wide range of test subjects and steps. Regression methods are then used to provide suitable estimates. Much work in this area appears to use step frequency alone, although variance of the accelerometer data is often added. Some regression approaches are linear, but others allow for non-linear combinations or are non-parametric such as using neural networks.

One of the techniques reviewed by Diaz et. al. was described by S. H. Shin, C. G. Park, J. W. Kim, H. S. Hong, and J. M. Lee, "Adaptive step length estimation algorithm using low-cost MEMS inertial sensors," in Proc. IEEE Sens. Appl. Symp. (SAS), February 2007, pp. 1-5. In this example, a combination of step frequency and accelerometer variance are used to infer the step length. The authors found it necessary to classify the motion as walking or running with two linear relationships between step frequency and step length.

Another of the techniques reviewed by Diaz et. al. was described by J.-S. Hu, K.-C. Sun, and C.-Y. Cheng, "A kinematic human-walking model for the normal-gait-speed estimation using tri-axial acceleration signals at waist location," IEEE Trans. Biomed. Eng., vol. 60, no. 8, pp. 2271-2279, August 2013. In this example, more biomechanically driven algorithms were described that used data from waist mounted sensors and a so-called 'inverted pendulum model' in which the centre of mass of the user is considered to be moving as an inverted pendulum, as a step progresses. This technique is, however, more focussed upon the gait speed rather than the step length.

Another of the techniques reviewed by Diaz et. al. was referred to by H. Weinberg (2002), "Using the ADXL202 in Pedometer and Personal Navigation Applications', Analog Devices Application Note, AN-602. This example estimates step length using an individual multiplicative calibration factor applied to the fourth root of the range of the vertical acceleration during the step and is possibly the most similar to the technique described in WO/2015/079260.

Diez et. al., indicates that particularly accurate solutions to step length estimation use sensor units mounted on a foot. These can use zero-point updates (ZUPTs) when the foot is stationary on the ground, to stabilise a Kalman-filter processing the IMU data, allowing the use of double integration of horizontal acceleration to estimate step length very accurately. However, such techniques are not appropriate for many applications since the wearing of a sensor on a user's foot can be impractical. Generally, for ease of use, versatility and general practicality it is better to use a sensor mounted at (or near) the hip or at some other location close to or on the torso of a user. For example, for a smartphone based application that uses internal inertial sensors it is not generally appropriate to position the smartphone on the foot.

Accordingly, for systems such as WO/2015/079260, and similar systems, that are typically optimised for use with smart phone IMU units attached to a user's hip, it is apparent that an approach to step length estimation is desirable that is more versatile than approaches requiring a foot mounted sensor, but is nevertheless sufficiently accurate in terms of step detection and step length calculations.

The system of WO/2015/079260 processes the IMU data by applying a Kalman filter. This allows orientation to be tracked and aids step detection. Upon detection of a step, a step update is invoked in the particle filter. In this, particles are moved using estimates of the step length and heading, with some noise added to cover the uncertainty. In environments with lots of structure this is sufficient for to provide good tracking. Large amounts of noise can be applied to individual steps to deal with variation in step length, as bad particles will frequently be killed off by wall collisions.

However, whilst the system of WO/2015/079260 generally provides sufficiently accurate data, in some scenarios, such as in large open spaces or long uninterrupted corridors, adding large amounts of noise per step can cause particles to spread out over time to the point that there is an insufficient particle density to cover the true state. Conversely, lower noise can result in confidently predicting the wrong location of a particle if there is a significant change in step length, for example as someone speeds up or slows down, or starts walking on an incline.

It can be seen, therefore, that it would be desirable to be able to predict the step length of a user more accurately, on a step to step basis, so that lower noise can be used, and more accurate and robust predictions of position provided.

The present invention is therefore concerned with providing apparatus and methods for providing improvements in step length estimation generally and in particular, but not limited to, providing improvements in step length estimation for use with waist mounted sensors and systems such as that described in WO/2015/079260.

Accordingly, preferred embodiments of the present invention aim to provide methods and apparatus which at least partially contribute to providing such improvements in step length estimation.

SUMMARY OF THE INVENTION

In one aspect the invention provides a method for estimating a step length of a user, the method comprising: obtaining inertial data generated by at least one inertial sensor; extracting, from the inertial data, orthogonal motion components in at least two directions; estimating, based on the orthogonal motion components for each direction, a respective parameter that is indicative of energy expenditure by the user in the corresponding direction; and estimating, based on each estimated parameter that is indicative of energy expenditure by the user, a corresponding step length.

The orthogonal motion components may be extracted using at least one filter (for example using at least one Kalman filter). The orthogonal motion components may be smoothed using one or more high pass filters.

The orthogonal motion components in at least two directions are, advantageously, orthogonal in a plane perpendicular to a gravitational direction (i.e. a horizontal plane).

The orthogonal motion components may comprise orthogonal acceleration components. The estimating of parameters that are indicative of energy expenditure by the user may thus be based on orthogonal velocity components that are extracted from the orthogonal acceleration components. The orthogonal motion components may comprise orthogonal velocity components.

Each parameter that is indicative of energy expenditure by the user in the corresponding direction may be approximated by applying a window function to a respective set of the orthogonal velocity components in the corresponding direction for a time period corresponding to the window function. The window function may, for example, comprise a generalised cosine window, optionally a Hamming window or other similar window. Each parameter that is indicative of energy expenditure by the user in the corresponding may be approximated based on a calculation of a variance with this window function. For example, each parameter that is indicative of energy expenditure by the user in the corresponding direction may be a power parameter, P, (or similar) that is estimated using a mathematical model, equation or function. For example, for a window function of length n, the power parameter may be estimated using the following equation:

$$P = \left( \sum_{i=1}^{n} \left( v_i^2 \times \frac{h_i}{\sum_{i=1}^{n} h_i} \right) - \left( \sum_{i=1}^{n} \left( v_i \times \frac{h_i}{\sum_{i=1}^{n} h_i} \right) \right)^2 \right)$$

wherein, $h_i$ is the coefficient given by the window function at time point i in the n length window function, and $v_i$ is the estimated instantaneous velocity component at time point i in the n length window function.

The estimating of the corresponding step length may comprise estimating the corresponding step length based on a mathematical model that maps the sum of respective orthogonal estimated parameters that are indicative of energy expenditure by the user, in each of at least two orthogonal directions, to an estimated step length, based, for example, on at least one mapping parameter.

The at least one mapping parameter comprises a coefficient, k, a power, $1/\alpha$, and an offset, and wherein the mathematical model may provide an estimated step length, $SL_{uncal}$, given by: $SL_{uncal} = k \times (P_N + P_E)^{1/\alpha} - \text{offset}$; where $P_N$ and $P_E$ are the respective orthogonal estimated parameters in each of each of two orthogonal directions (e.g. nominally North and East power components).

The least one mapping parameter may comprise at least one population specific parameter that is derived from previously extracted data representing typical locomotory motion for a given population of a number of users.

The method may further comprise: identifying a population specific profile from a plurality of selectable population specific profiles, wherein each selectable population specific profile comprises at least one respective population specific parameter that is different from a corresponding population specific parameter in another of the plurality of selectable population specific profiles; and estimating the corresponding step length based on the mathematical model using, as the at least one mapping parameter, at least one population specific parameter from the identified population specific profile.

The estimated step length may be an initial step length and the method may further comprise deriving an estimated user specific step length by applying, to the initial estimate of step length, a user specific parameter, that is derived from previously extracted data representing locomotory motion of the user.

In one aspect the invention provides apparatus for estimating a step length of a user, the apparatus comprising: means for obtaining inertial data generated by at least one inertial sensor; means for extracting, from the inertial data, orthogonal motion components in at least two directions; means for estimating, using the orthogonal motion components for each direction, a respective parameter that is indicative of energy expenditure by the user in the corresponding direction; and means for estimating, using each estimated parameter that is indicative of energy expenditure by a user, a corresponding step length.

The means for obtaining inertial sensor may be configured to obtain the inertial data from at least one body worn inertial sensor (e.g. on worn on a user's torso at the waist, chest or hip).

Aspects of the invention extend to computer program products such as computer readable storage media having instructions stored thereon which are operable to program a programmable processor to carry out a method as described in the aspects and possibilities set out above or recited in the claims and/or to program a suitably adapted computer to provide the apparatus recited in any of the claims.

Each feature disclosed in this specification (which term includes the claims) and/or shown in the drawings may be incorporated in the invention independently (or in combination with) any other disclosed and/or illustrated features. In particular but without limitation the features of any of the claims dependent from a particular independent claim may be introduced into that independent claim in any combination or individually.

BRIEF DESCRIPTION OF THE SEVERAL VIEWS OF THE DRAWINGS

Embodiments of the invention will now be described by way of example only with reference to the attached figures in which.

DESCRIPTION OF SPECIFIC EMBODIMENTS OF THE INVENTION

A portable device for detecting, and estimating the length of steps taken by a user carrying the device is described by way of example with reference to the drawings. The portable device generates an estimate of the step length based on derived power parameters that are indicative of the power (energy expended per unit time) being expended by a user of the device. The derived power parameters are determined based, ultimately, on estimates of oriented inertial data extracted from raw inertial data output by one or more inertial sensors provided in the portable device.

The method used for estimating step length, in the portable device, is based on the premise that for a given person, walking faster generally involves walking in a more 'energetic' manner. Thus, identification of higher and lower energy steps can be used to allow an estimated step length to be scaled up or down based on an estimate of the energy expended.

Even if a given estimate of a step length for an individual step might be relatively inaccurate, for many systems (such as, but not limited to, those involving use of a particle filter), this is of less concern than the ability to take into account a systematic change in a user's locomotory style (e.g. walking, jogging, running, ascending, descending, etc.) over a number of steps with resulting greater accuracy in an estimate of the distance travelled over a number of steps while the change in walking style occurs.

This difference in emphasis has led to a significantly different step estimation procedure then has previously been employed in many existing systems.

Figure 1:
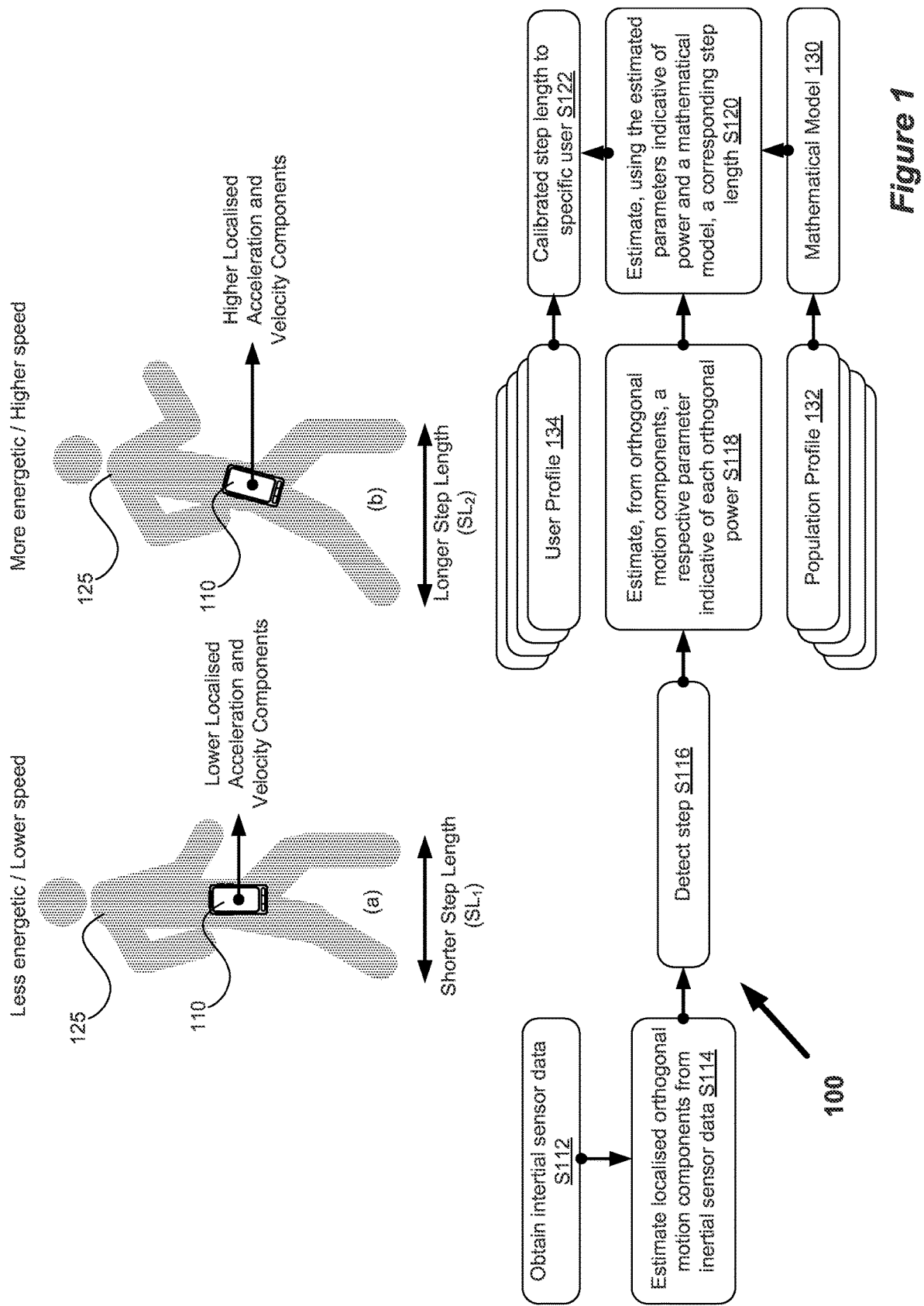
FIG. 1 schematically illustrates, in simplified form, a method for obtaining step length estimates in overview.

FIG. 1 schematically illustrates a simplified overview of the step length estimation method generally at 100. The step length estimation method 100 is employed in a portable device 110 that incorporates a suitable form of inertial sensor and which, in this example, is worn on the waist of a user 125. The inertial sensor, in this example, comprise a multi-axis (e.g. three orthogonal axes) accelerometer for measuring linear acceleration in different directions, gyroscope for measuring rotation around three different axes and magnetometers for measuring the magnetic field in different direction (although any suitable inertial sensors may be used).

In FIG. 1, the step length estimation method 100 accurately detects steps, and estimates step lengths, for users using different locomotory styles or for a user that moves between one style and another. As seen in FIG. 1, by way of example only, the user 125 is shown using two different locomotory styles: a first style (a) in which the user is moving at a relatively low, less energetic, speed (e.g. walking) using relatively short step lengths ($SL_1$); and a second style (b) in which the user is moving at a relatively fast, more energetic, speed (e.g. running or jogging) using relatively longer step lengths ($SL_2$).

During the first style of locomotion (a), the user's waist (and hence the device 110) will exhibit localised movement (movement relative to the underlying more systematic movement of the user in a particular direction) that has lower acceleration and velocity components compared to the second style of locomotion (b).

The step length estimation method 100 beneficially exploits these differences to provide step length estimates that automatically and dynamically adjust for such different styles of locomotion without requiring separate detection of a change in gait and an associated switching between different locomotion profiles.

Specifically, the step length estimation method 100 involves continuously obtaining associated acceleration data from the inertial sensor(s) at S112.

The step length estimation method 100 then applies appropriate data/signal processing, at S114, to the received raw inertial data in order to extract estimates of localised two dimensional (2D) 'horizontal' motion (in this example velocity) components in orthogonal (e.g. North and East) directions.

As will be described in more detail later, the processing, in this example, involves the application of appropriate filtering to the raw data (e.g. using a stabilised strapdown Kalman or similar filter) to first produce an estimate of oriented inertial data in the form two dimensional (2D) acceleration components in orthogonal (e.g. North and East) directions. The orientated acceleration components, in this example, may then be filtered (if necessary) to produce smoothed acceleration signals in which the effect of any accelerometer bias or gravity leakage is removed or at least significantly inhibited. The (smoothed) orthogonal horizontal acceleration components are then integrated in the horizontal (e.g. North and East) axes to provide the horizontal velocity components which may also be filtered (if necessary) to produce smoothed localised orthogonal velocity components.

In this example, when a user makes a step, the step is detected as S116 based on the oriented sensor data arising from S114. It will be appreciated however that other step detection methods are possible that do not use the oriented sensor data in this way.

The step length estimation method 100 proceeds, when a step is detected at S116, with the application, at S118, of appropriate signal/data processing to the (smoothed) orthogonal motion (e.g. velocity) components to obtain respective parameters that are indicative of power (and hence energy consumption) in each orthogonal direction. In this example these parameters are referred to as 'velocity powers'.

At S120, a mathematical model 130 is then applied, to a combination of both of the orthogonal velocity powers estimated at S118, to map the combined velocity power to a population specific estimated step length (i.e. the step length would remain the same, for the same velocity based input data, for any user of a given population of users).

It will be appreciated that whilst the underlying mathematical model 130 may remain the same for different populations of users the model 130 has a number of parameters that can, beneficially, be adjusted to improve the model 130 over time or to tailor it to take account of differences in step characteristics exhibited by different populations. For example, a population of athletes may be expected to have different step characteristics compared to a population representing average members of the public. Similarly a population with an unusually tall average height may be expected to have a different step characteristics compared to a population with an unusually short average height.

Optionally, therefore, each set of population specific parameters can form a respective population specific profile 132 that can be used as an input to the mathematical model to ensure that the step length estimates are appropriate tailored to a population that the user of the device forms part of.

Similarly, different population specific profiles 132 could be generated for different sensor placements. For example, one population specific profile 132 could be generated for a population of users that has the sensor located at the waist whereas another population specific profile 132 could be generated for a population of users that has the sensor located elsewhere on the body (e.g. near the chest in a jacket pocket) or on the head (e.g. built into a virtual reality headset, glasses, headphones or other headgear).

Where the step length method is implemented for a device that may be located (or has inertial sensors that may be located) in any of number of different locations (e.g. as part of an application on a smartphone), the population specific profile may be user configurable. For example, the user may be provided with an option in a settings menu of an application to set the location to any of a plurality of different possible locations each of which has a different respective population specific profile associated with it.

In this example, the population specific estimated step length provided at S120 is also be adjusted, at S122 (if necessary) to provide a user specific step length that is calibrated, based on user specific calibration data, to take account of user specific step characteristics (e.g. an unusually long or short step length) within the population. Optionally, therefore, user specific calibration data for each user can form part of a respective user specific profile 134 that can be used as an input to the calibration step S122 of the step length estimation method 100 in order to provide more accurate user specific step length estimation.

Thus, it can be seen that the above techniques can be combined through a map-matched particle filtering approach with motion analysis and classification with the potential to make inertial-only indoor tracking technically feasible in a much wider range of applications.

Step Length Estimation Device

Figure 2:
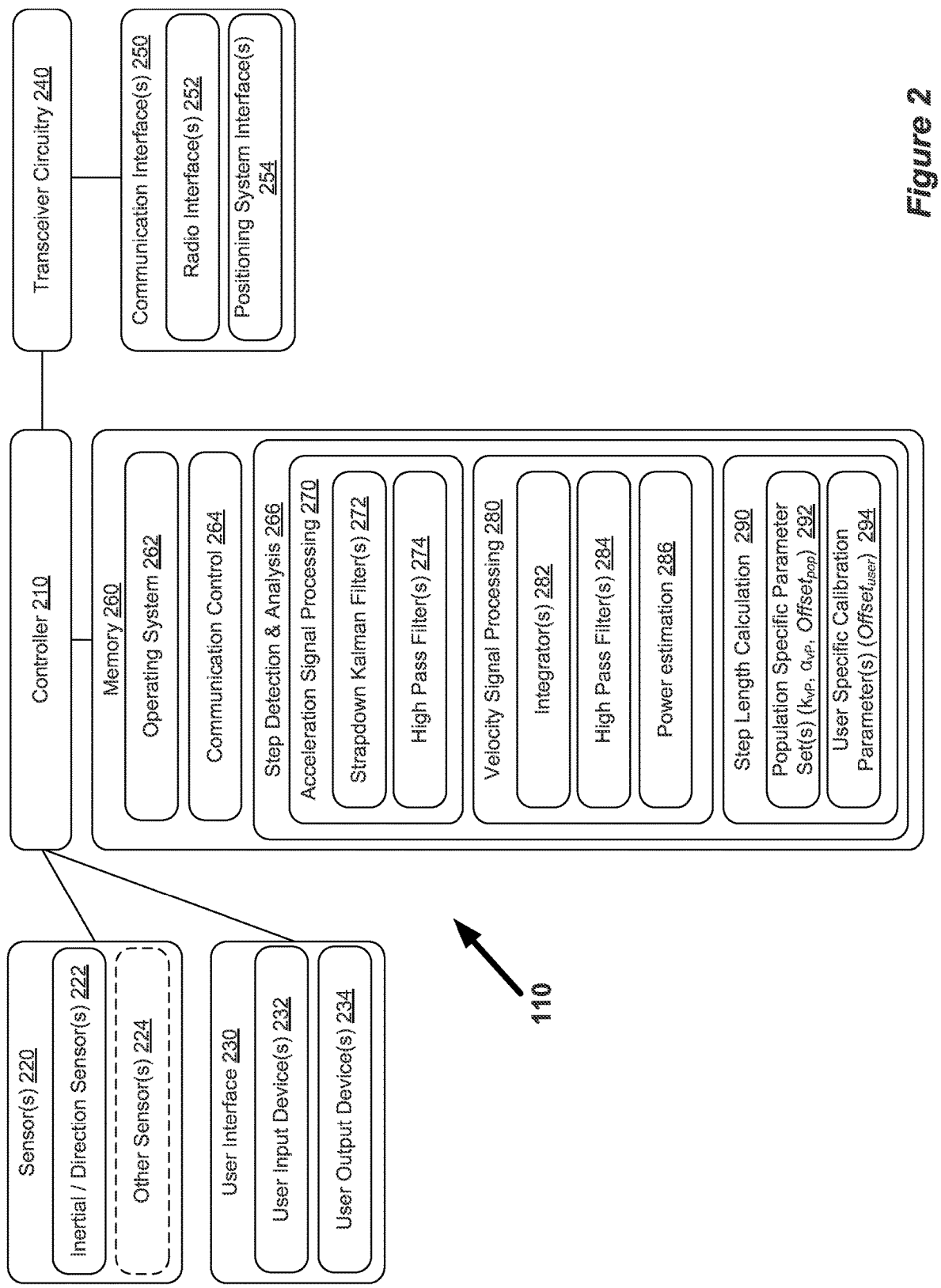
FIG. 2 schematically illustrates apparatus embodying the step length estimating method of FIG. 1.

FIG. 2 is a simplified block diagram illustrating user equipment 110 in which the location the step length estimation method 100 of FIG. 1 may be implemented for estimating user step/stride length. It will be appreciated that the user equipment illustrated in FIG. 2 is purely exemplary, representing just one type of device in which the method may be implemented. The method of FIG. 1 may, of course, be implemented in any suitable device.

As shown, the user equipment 110 comprises a controller 210 for controlling the overall operation of the user equipment 110. The controller 210 is coupled to one or more sensors 220, a user interface 230, transceiver circuitry 240 with associated communication interfaces 250, and a memory 260.

Although not necessarily shown in FIG. 2, the user equipment 110 may of course have all the usual functionality of a conventional smartphone or other smart device and this may be provided by any one or any combination of hardware, software and firmware, as appropriate. Software may be pre-installed in the memory 260 and/or may be downloaded via a telecommunications network or from a removable data storage device (RMD), for example.

The sensor(s) 220 comprise one or more inertial/direction sensors 222 for sensing motion and orientation and for providing associated data from which the user equipment 110 can analyse and classify user motion appropriately, for example by determining when a step is taken, estimating a step length of the user over one or multiple steps, and calculate an associated bearing. The inertial/direction sensors 220, in this example, comprise a multi-axis (e.g. three orthogonal axes) accelerometer for measuring linear acceleration in different directions, one or more gyroscopes for measuring angular velocity, and a magnetometer based direction sensor. It will be appreciated, however, that any suitable inertial sensors may be used and that it may not be necessary for all such sensors to be present.

Where the user equipment 110 is only required to track movement in substantially two-dimensions, the inertial sensors 222 may be sufficient to achieve this. Such two-dimensional tracking may, for example, be sufficient in a building where there is little or no level ambiguity (e.g. a single floored building), or in a multi-floored building where movement around each floor is tracked separately in two-dimensions with an external input (e.g. from a user or a beacon) used to confirm which floor the user is on (and hence which floor plan representation to use from the mapping data). However, where the device 110 may be required to track movement in three-dimensions the sensors 220 may comprise one or more other sensors 224 (e.g. a pressure sensor or the like) to provide motion/position related data representing altitude (movement up/down in a 'z' direction orthogonal to the x and y directions). Other sensors 224 that may be provided for the user equipment 110 may, alternatively or additionally, include any other suitable externally connected or internal sensor for providing associated sensor data (e.g. a temperature sensor, infra-red sensor, light sensor, camera and/or the like).

The user interface 230 comprises user input devices 232 for receiving input from the user and user output devices 234 for providing output to the user. The user input devices 232 may comprise any suitable input devices including, for example, one or more audio input devices (e.g. a microphone), a touch sensitive display, one or more function keys/buttons, a fixed keypad, a camera and/or the like. The user output devices 234 may comprise any suitable output devices including, for example, one or more audio output devices (e.g. a speaker), a visual display (which may be provided by a touch sensitive display), one or more light sources (e.g. a camera flash), one or more sources of tactile feedback (e.g. a vibration generator) and/or the like.

The transceiver circuitry 240 is operable to transmit signals to, and to receive signals from, one or more other communication devices via one or more corresponding communication interfaces 250 and associated antenna. In this example, the user equipment 110 comprises one or more radio interfaces 252 via which communication to/from other radio communication enabled devices can be made, and one or more positioning system interfaces 254 for acquiring global positioning system (GPS) signals (or other similar positioning signals) which the user equipment 110 can analyse to providing associated measurement/position data. The radio interface(s) 252 may, for example, be configured for facilitating: communication via cellular base stations with other similar user equipment; communicating with radio beacons forming part of a location system for enhanced location tracking; near field, Wi-Fi, and/or Bluetooth communication; and/or the like.

The controller 210 is configured to control the overall operation of the user equipment 110 by, in this example, program instructions or software instructions stored within the memory 260. As shown, these software instructions include, among other things, an operating system 262, a communications control module 264, and a step detection and analysis module 266.

The communications control module 262 controls transmission and receipt of user equipment 110 communications from and to the other communication entities such as cellular base station, Wi-Fi access points, radio beacons, positioning system entities (e.g. satellites) etc.

The step detection and analysis module 266 is configured to detect steps made by the user from inertial data provided from the inertial sensors 222 and to process the inertial data to implement the step length estimation method 100 of FIG. 1. To facilitate implementation of the step length estimation method 100 the step detection and analysis module 266 includes a number of sub-modules. In this example, the sub-modules comprise (but are not limited to) an acceleration signal processing module 270, a velocity signal processing module 280, and a step length calculation module 290.

The acceleration signal processing module 270 is configured to process acceleration data from the inertial sensors 222 using appropriate acceleration signal processing filters 272, 274. As shown in FIG. 2 and described in more detail with reference to FIG. 3, in this example the acceleration filters 272, 274 comprise one or more Kalman filters 272 (in the figure stabilised strapdown Kalman filter(s)) and one or more high pass filters 274.

The velocity signal processing module 280 is configured to generate velocity data from the acceleration data provided by the inertial sensors 222 by means of one or more integrator(s) 282, to process the generated velocity data using one or more velocity signal processing filters 284, and to calculate estimated velocity powers using a power estimation module 286. As shown in FIG. 2 and described in more detail with reference to FIG. 3, in this example the velocity filter(s) 284 comprises one or more high pass filters 284.

The step length calculation module 290 is configured to calculate estimates of a population step length for an average member of a given user population based on the velocity power estimates and a population specific parameter set 292 stored in the memory 260 (and that forms a corresponding population profile 132 shown in FIG. 1) for that user population. Where at least one user specific calibration parameter 294 is available (e.g. stored in the memory 260) for the specific user of the user equipment 110 (e.g. at least one parameter 294 that forms a corresponding user profile 134 shown in FIG. 1), the step length calculation module 290 is also configured to determine an estimated user specific estimate of a step length that is calibrated based on the associated user specific calibration parameter(s) 294.

In the example described above, the user equipment includes transceiver circuitry. Typically this circuitry will be formed by dedicated hardware circuits. However, in some embodiments, part of the transceiver circuitry may be implemented as software run by the corresponding controller.

In the above example, a number of software modules, sub-modules filters and other functions were described as being stored in the memory. As those skilled in the art will appreciate, these modules, sub-modules, filters and functions may be provided in compiled or un-compiled form and may be supplied to the user equipment as a signal over a computer network, or on a recording medium. Moreover whilst these modules, sub-modules, filters and functions may be provided in this way for certain applications, for example where an existing system has been modified to implement the step length calculation method, in other applications, for example in systems designed with the features described in mind from the outset, these modules, sub-modules, filters and functions may be built into the overall operating system or code and so these modules, sub-modules, filters and functions may not be discernible as discrete entities. Further, the functionality performed by part or all of the software may be performed using one or more dedicated hardware circuits.

Step Length Estimation

Figure 3:
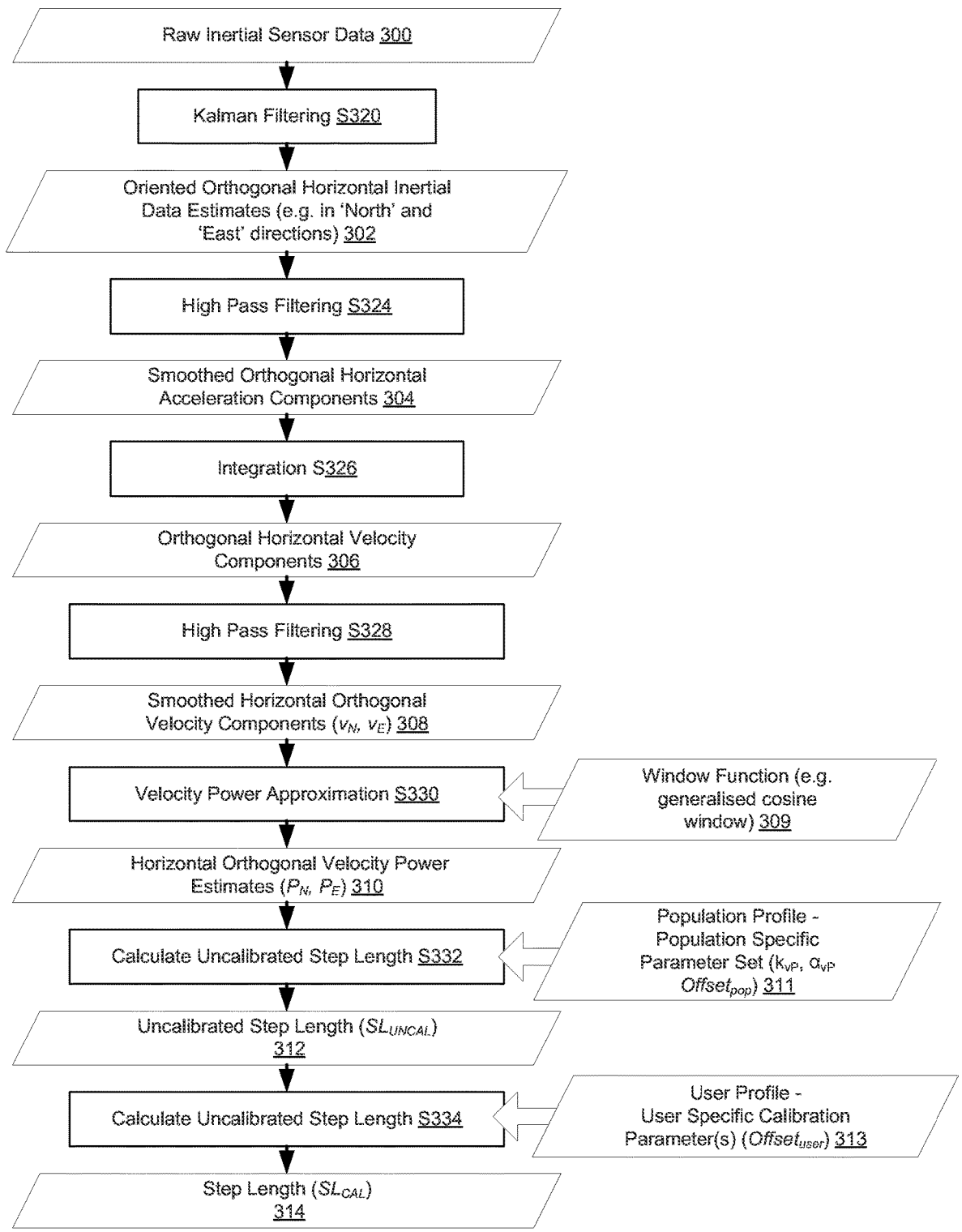
FIG. 3 is a simplified flow chart illustrating operation of the apparatus of FIG. 2, in more detail, estimate step lengths.

FIG. 3 is a simplified flow chart illustrating one possible implementation of the step length estimation method 100 of FIG. 1 in greater detail. It will be appreciated that other implementations are possible in which some of the steps are modified or even omitted.

As seen in FIG. 3, the procedure falls broadly into the following stages:

1. Kalman filtering (S320) which involves application of a stabilised strapdown Kalman filter to raw inertial data to obtain oriented inertial data.
2. Obtaining horizontal velocity estimates (S324, to S328) which involves integration and filtering of acceleration data in horizontal (North and East) axes to get horizontal velocities and the filtering of the horizontal velocities.
3. Obtaining velocity powers (S330) which involves summing the power in horizontal velocities by taking the variance over a one second hamming window.
4. Calculating an uncalibrated step length (S332) which involves taking the sum of horizontal velocity powers in orthogonal directions to a population specific power (in this example a decimal or fractional power ($1/\alpha_{v,P}$)), multiplying by a population specific coefficient ($k_{v,P}$) and subtracting a population specific offset ($Offset_{pop}$) to provide the uncalibrated step length in metres.
5. Calculating a calibrated (user specific) step length (S334) by adding a user specific, individually calibrated, calibration length offset ($Offset_{user}$) to the uncalibrated step length.

These stages will now be described in more detail, by way of example only, with reference to FIG. 3.

Kalman Filtering

As seen in FIG. 3 at S320 raw inertial sensor data (acceleration data) 300 is filtered to produce estimates 302 of orthogonal acceleration components (e.g. North and East components) in the horizontal plane (i.e. the plane perpendicular to the direction of gravity) using a Kalman filter. Any suitable filter may be used, for example any suitable strapdown Kalman filter, to produce an estimate of the orientated inertial data. In order to produce reasonable estimates of orthogonal acceleration components it is sufficient that the orientation is reasonably stable, and the vertical orientation (i.e. in the gravitational direction) is determined accurately.

Thus, the Kalman filter provides accelerometer signals that have been transformed into the orthogonal (North and East) components 302.

In the method described a 15-state error-state Kalman filter is used with periodic stabilising zero-position observations. Whilst this leads to a solution which may be less accurate over short periods of time than one without the zero-position observations it tends to provide improvements in long-term orientation and position stability. Specifically, if a user is stationary, then periodically (e.g. every second or so) the Kalman filter is passed a weak observation indicating that the user has not moved. Since all sources of drift (e.g. arising from accelerometer bias and/or gravity leakage) can lead, eventually, to relatively large position errors building up, the use of the zero-position observations have the effect of gently eliminating the sources of drift albeit at the cost of the filter itself not returning a meaningful position or velocity estimate. Nevertheless, for heading, orientation and local velocity changes (which is what the proposed step length estimation method uses) this technique is sufficient.

Obtaining Horizontal Velocity Estimates

The estimated oriented orthogonal (North and East) horizontal accelerometer components 302 are continually filtered at S324 using any suitable filter(s) (in this example high pass filter(s)) to produce smoothed orthogonal acceleration signal components 304 for which any accelerometer bias and/or gravity leakage has been eliminated or at least significantly inhibited.

The smoothed acceleration signal components 304 are then integrated at S326 (e.g. by means of the integrator(s) 282 of FIG. 2), to produce an output in the form of orthogonal horizontal velocity components 306. The orthogonal horizontal velocity components 306 are also continually filtered, at S328, using any suitable filter(s) (in this example high pass filter(s)) to produce smoothed orthogonal velocity components 308 ($v_N$, $v_E$) in the horizontal plane.

The filters used for smoothing the acceleration and velocity signals are, in this example, 2-tap Butterworth infinite impulse response (IIR) filters designed with a 0.005 fractional cut-off (3 dB point) frequency for 100 Hz signals. Nevertheless, many similar filters could be used in their place, or a single filtering/integration operation combining both the filtering and integration could be used.

It will be appreciated, that although the outputs are referred to as estimates of "horizontal velocity components" they represent locally accurate estimates of velocity as any unchanging or slowly changing systematic components (referred to as "direct current" (DC) components) of the velocity signal are, in effect, removed or at least significantly suppressed by the filtering.

Obtaining Velocity Powers

The estimated horizontal velocity components 308 ($v_N$, $v_E$) are stored in a rolling buffer of length $T_{buffer}$ (a buffer of 1-second length is typically sufficient). On detection of a step the most recent of these (i.e. those in the most recent $T_{buffer}$ period) are used to calculate estimates of the orthogonal power components 310 ($P_N$, $P_E$) at S330.

The power estimation is approximated, for each of the orthogonal directions, by respective calculation of the variance with a length 'n' window function 309 (in this example a generalised cosine window such as a Hamming window or the like) with coefficients $h_i$. The respective power P in each orthogonal direction is estimated as:

$$P = \left( \sum_{i=1}^{n} \left( v_i^2 \times \frac{h_i}{\sum_{i=1}^{n} h_i} \right) - \left( \sum_{i=1}^{n} \left( v_i \times \frac{h_i}{\sum_{i=1}^{n} h_i} \right) \right)^2 \right)$$

Where $v_i$ is the instantaneous velocity component (for the orthogonal direction in question) at time point i in the n length window.

It will be appreciated that the power parameters P need not represent an accurate estimate of actual power but can simply provide a systematically consistent indication of the power for different locomotory styles.

Calculating an Uncalibrated Step Length

At S332, the uncalibrated step length 312 ($SL_{UNCAL}$) is calculated, based on a sum of the orthogonal power components ($P_N$, $P_E$) and a population specific parameter set 311/profile 132 comprising the population specific denominator of the population specific decimal or fractional power ($1/\alpha_{vP}$), the population specific coefficient ($k_{vP}$) and the population specific offset ($Offset_{pop}$) as follows:

$$SL_{uncal} = k_{vP} \times (P_N + P_E)^{1/\alpha_{vP}} - Offset_{pop}$$

A set of parameters found to be particularly accurate both for a specific population of users and more generally for the wider population is:

A population specific decimal or fractional power of $1/10$ or $0.1$ (i.e. $\alpha_{vP} = 10$);

A population specific coefficient ($k_{vP}$) of 3; and

A population specific offset ($Offset_{pop}$) of 1.3

This population specific parameter set was derived for a population of eighteen users specifically selected to present a range of different body types and walking styles as gauged by gender, height, weight, age and fitness. The selected users took part in a trial in which each user walked in a straight line over a set distance multiple times at different speeds, ranging from a very slow shuffle to a brisk power walk. The number of steps taken for each pass was then counted and an average step length estimated based on this.

The data from fifteen of the users was used for determining the population specific parameter set and the data from the other three users was used independently for validation of the parameter set.

It was found that the resulting population specific parameter set provided sufficient correlation between the results provided by the simple metric for uncalibrated step length 312 ($SL_{UNCAL}$) described above using the inertial data, and the actual average step length calculated for the trial group.

Accordingly, this approach produces an estimate that is reasonably accurate for the general population.

Calculating a Calibrated (User Specific) Step Length

Nevertheless, the estimate can be further improved significantly by applying, at S334, an individual (user specific) calibration offset 313 ($Offset_{user}$) to the uncalibrated step length 312 ($SL_{UNCAL}$) to determine a calibrated (user specific) step length 314 ($SL_{CAL}$). Specifically, an individual's calibrated step length is produced by adding the individual (user specific) calibration offset 313 ($Offset_{user}$)—which may be negative or positive—to the uncalibrated step length 312 ($SL_{UNCAL}$) as follows:

$$SL_{cal} = SL_{uncal} + Offset_{user}$$

The individual (user specific) calibration offset 313 ($Offset_{user}$) can be calculated using a fairly straightforward initial calibration procedure in which the user's steps are counted as the user walks a short, known length, path and the actual average step length calculated. The uncalibrated step length is then calculated as described above with reference to FIG. 3 and the offset that would have led to the actual average length determined.

However, it will be appreciated that other methods could be used in addition or as an alternative to using a separate initial calibration procedure, for example methods involving ongoing ('dynamic') assessment and refinement of the calibration offset based on journeys made by the user when walking with a good GPS signal.

MODIFICATIONS AND ALTERNATIVES

Detailed embodiments have been described above. As those skilled in the art will appreciate, a number of modifications and alternatives can be made to the above embodiments whilst still benefiting from the inventions embodied therein.

The portable device in which the step length estimation method is used may be a stand-alone dedicated tracking device or may be integrated as part of another device. For example, the portable device may form part of a dedicated fitness tracker device or part of more generic user equipment (UE) for a cellular or similar network for example, a mobile communications device such as a mobile (cellular) telephone, smartphone, personal digital assistant, laptop, notebook, tablet computer, and/or the like.

It will be appreciated that whilst the described method is particularly advantageous for devices/sensors worn at the waist (or elsewhere on the torso) of a user, the method can, nevertheless, be adapted to provide advantageous step length estimation for devices that are worn at (or that receive inertial data from sensors that are worn at) other positions on a user's body. Such a method can, for example, provide advantages in any application in which as user's walking style may change dynamically over time—especially over a number of steps during such a dynamic change of walking style.

It will be appreciated that whilst in some devices the inertial sensor may be integrated together in the same device as a processor (or dedicated circuitry) configured to implement the step length estimation method, the sensor may be provided remotely and may provide the inertial data that it generates via a wireless or wired connection.

In the above description, the controller 210 is described for ease of understanding as having a number of discrete software modules. However, it will be appreciated that the functionality performed by part or all of the software may be performed using one or more dedicated hardware circuits for example using one or more dedicated integrated circuits such as an application specific integrated circuit (ASIC) or the like. The use of software modules is, nevertheless, preferred as it facilitates the updating of the step length estimation method.

It will be appreciated that the controller 210 referred to in the description may comprise any suitable controller such as, for example an analogue or digital controller. Each controller may comprise any suitable form of processing circuitry including (but not limited to), for example: one or more hardware implemented computer processors; microprocessors; central processing units (CPUs); arithmetic logic units (ALUs); input/output (IO) circuits; internal memories/caches (program and/or data); processing registers; communication buses (e.g. control, data and/or address buses); direct memory access (DMA) functions; hardware or software implemented counters, pointers and/or timers; and/or the like.

Various other modifications will be apparent to those skilled in the art and will not be described in further detail here.

The invention claimed is:

1. A method for estimating a step length of a user, the method comprising:
   obtaining inertial data generated by at least one inertial sensor;
   extracting, from the inertial data, orthogonal motion components in at least two directions;
   estimating, based on the orthogonal motion components for each direction, a respective parameter that is indicative of energy expenditure by the user in the corresponding direction; and estimating, based on each estimated parameter that is indicative of energy expenditure by the user, a corresponding step length;

wherein the orthogonal motion components comprise orthogonal acceleration components, and the estimating of parameters that are indicative of energy expenditure by the user is based on orthogonal velocity components that are extracted from the orthogonal acceleration components.

2. A method as claimed in claim 1, wherein the orthogonal motion components are extracted using at least one filter.

3. A method as claimed in claim 2, wherein the orthogonal motion components are extracted using at least one Kalman filter.

4. A method as claimed in claim 2, wherein the orthogonal motion components are smoothed using at least one high pass filter.

5. A method as claimed in claim 1, wherein the orthogonal motion components in at least two directions are orthogonal in a plane perpendicular to a gravitational direction.

6. A method as claimed in claim 1, wherein the orthogonal motion components comprise orthogonal velocity components.

7. A method as claimed in claim 1, wherein each parameter that is indicative of energy expenditure by the user in the corresponding direction is approximated by applying a window function to a respective set of the orthogonal velocity components in the corresponding direction for a time period corresponding to the window function.

8. A method as claimed in claim 7, wherein the window function comprises a generalised cosine window.

9. A method as claimed in claim 7, wherein each parameter that is indicative of energy expenditure by the user in the corresponding direction is approximated based on a calculation of a variance with the window function.

10. A method as claimed in claim 9, wherein each parameter that is indicative of energy expenditure by the user in the corresponding direction is a power, P, that is estimated, for a window function of length n, using the following equation:

$$P = \left( \sum_{i=1}^{n} \left( v_i^2 \times \frac{h_i}{\sum_{i=1}^{n} h_i} \right) - \left( \sum_{i=1}^{n} \left( v_i \times \frac{h_i}{\sum_{i=1}^{n} h_i} \right) \right)^2 \right)$$

wherein, $h_i$ is the coefficient given by the window function at time point i in the n length window function, and $v_i$ is the estimated instantaneous velocity component at time point i in the n length window function.

11. A method as claimed in claim 1, wherein the estimating of the corresponding step length comprises estimating the corresponding step length based on a mathematical model that maps:

the sum of respective orthogonal estimated parameters that are indicative of energy expenditure by the user, in each of at least two orthogonal directions;

to an estimated step length;

based on at least one mapping parameter.

12. A method as claimed in claim 11 wherein the at least one mapping parameter comprises a coefficient, k, a power, $1/\alpha$, and an offset, and wherein the mathematical model provides an estimated step length, SLuncal, given by:

$$SL_{uncal} = k \times (P_N + P_E)^{1/\alpha} - \text{offset}$$

where $P_N$ and $P_E$ are the respective orthogonal estimated parameters in each of each of two orthogonal directions.

13. A method as claimed in claim 10, wherein the at least one mapping parameter comprises at least one population specific parameter that is derived from previously extracted data representing typical locomotory motion for a population of a number of users.

14. A method as claimed in claim 13 further comprising: identifying a population specific profile from a plurality of selectable population specific profiles, wherein each selectable population specific profile comprises at least one respective population specific parameter that is different from a corresponding population specific parameter in another of the plurality of selectable population specific profiles; and estimating the corresponding step length based on the mathematical model using, as the at least one mapping parameter, at least one population specific parameter from the identified population specific profile.

15. A method as claimed in claim 1, wherein the estimated step length is an initial step length and wherein the method further comprises deriving an estimated user specific step length by applying, to the initial estimate of step length, a user specific parameter, that is derived from previously extracted data representing locomotory motion of the user.

16. Apparatus for estimating a step length of a user, the apparatus comprising:

at least one inertial sensor for obtaining inertial data generated by;

a processor configured for:

extracting, from the inertial data, orthogonal motion components in at least two directions, estimating, using the orthogonal motion components for each direction, a respective parameter that is indicative of energy expenditure by the user in the corresponding direction, and estimating, using each estimated parameter that is indicative of energy expenditure by a user, a corresponding step length;

wherein the orthogonal motion components comprise orthogonal acceleration components and the estimating is based on orthogonal velocity components that are extracted from the orthogonal acceleration components.

17. Apparatus as claimed in claim 16 wherein the at least one inertial sensor comprises at least one body worn inertial sensor.

18. A computer program product, comprising: a non-transitory computer-readable medium comprising instructions which, when executed by a computer, cause the computer to carry out the method of claim 1.

19. A method as claimed in claim 7, wherein the window function comprises a Hamming window.

* * * * *